United States Patent [19]

Liebl et al.

[11] Patent Number: 4,749,403
[45] Date of Patent: Jun. 7, 1988

[54] HERBICIDAL DERIVATIVES OF IMIDAZOLIDINONE AND IMIDAZOLIDINE THIONE

[75] Inventors: Rainer Liebl, Todtenweis; Reinhard Handte, Gablingen; Hilmar Mildenberger, Kelkheim; Klaus Bauer, Rodgau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 11,780

[22] Filed: Feb. 6, 1987

[30] Foreign Application Priority Data

Feb. 8, 1986 [DE] Fed. Rep. of Germany ....... 3604042

[51] Int. Cl.$^4$ .................... A01N 43/90; C07D 513/04
[52] U.S. Cl. ............................................ 71/90; 71/92; 540/578; 540/579; 544/48; 544/105; 546/278; 548/302; 548/319
[58] Field of Search ................. 548/319, 302; 546/278; 544/105, 58.5, 48; 540/579, 578; 71/92, 90

[56] References Cited

U.S. PATENT DOCUMENTS 4,578,107 3/1986 Imai ............................... 548/319 X

OTHER PUBLICATIONS

*Chemical Abstracts*, 70:3934p (1969) [Scott, J., et al., *Biochem. J.*, 1968, 109(2), 209-15].

*Primary Examiner*—Richard A. Schwartz
*Attorney, Agent, or Firm*—Curtis, Morris & Safford

[57] ABSTRACT

The compounds of formula I

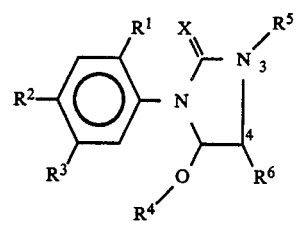

in which the substituents X, $R^1$, $R^2$, $R^3$, $R^4$, $R^5$, and $R^6$, are defined hereinbelow. The compounds have advantageous herbicidal properties and are useful, for example, for combating undesired plants.

5 Claims, No Drawings

HERBICIDAL DERIVATIVES OF IMIDAZOLIDINONE AND IMIDAZOLIDINE THIONE

Herbicides having an imidazolidinone structure are known from International patent application WO/01383. New derivatives of imidazolinone and imidazoline thione having advantageous herbicidal properties have now been found.

The present invention thus relates to compounds of the formula I

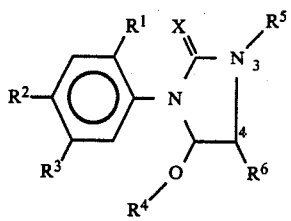

in which
X denotes oxygen or sulfur;
$R^1$ denotes hydrogen or halogen;
$R^2$ and $R^3$, independently of one another, denote hydrogen, halogen, $(C_1-C_4)$alkyl, halo$(C_1-C_4)$alkyl, $(C_1-C_4)$-alkoxy, halo$(C_1-C_4)$alkoxy, $(C_3-C_6)$cycloalkoxy, $(C_2-C_4)$-alkenyloxy, halo$(C_2-C_4)$alken $(C_3-C_4)$alkynyloxy, halo$(C_3-C_4)$alkynyloxy, $(C_1-C_4)$alkoxy $(C_1-C_4)$-alkoxy; $(C_1-C_4)$alkoxycarbonyl-$(C_1-C_4)$alkoxy-carbonyl, halo$(C_1-C_4)$alkoxycarbonyl, $(C_1-C_4)$alkylsulfinyl, $(C_1-C_4)$alkylsulfonyl; phenoxy, phenylthio, phenylsulfinyl or phenylsulfonyl, where the phenyl ring may in each case be mono- to trisubstituted by halogen, $(C_1-C_4)$alkyl, $CF_3$ or $NO_2$; pyridyloxy which may be mono- or disubstituted by halogen or $CF_3$; benzyloxy or phenoxymethyl, which may both be mono- to trisubstituted in the phenyl ring by halogen, $C_1-C_4$)alkyl, $(C_1-C_4)$alkoxy, $CF_3$ or $NO_2$; $(C_1-C_4)$alkoxycarbonyl, $(C_1-C_4)$alkoxycarbonyl$(C_1-C_4)$alkoxy, $(C_1-C_4)$alkylthio, $(C_1-C_4)$alkoxycarbonyl$(C_1-C_4)$alkylthio, $NO_2$ or CN, $R^4$ denotes hydrogen, $(C_1-C_4)$alkyl, halo$(C_1-C_4)$alkyl, $(C_3-C_4)$alkenyl, $(C_3-C_4)$cycloalkyl, $(C_5-C_6)$-cycloalkenyl, $(C_3-C_4)$alkynyl, $(C_1-C_4)$alkoxy$(C_1-C_4)$alkyl, $(C_1-C_4)$alkoxycarbonyl$(C_1-C_4)$-alkyl, $(C_1-C_4)$-alkylthio$(C_1-C_4)$alkyl; benzyl, which may be mono- to trisubstituted by halogen, $(C_1-C_4)$alkyl, $(C_1-C_4)$alkoxy, $(C_1-C_4)$alkoxycarbonyl, $CF_3$, $NO_2$ or CN, or denotes a radical of the formula

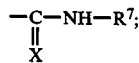
—C—NH—R$^7$;
‖
X $R^5$ denotes hydrogen, $(C_1-C_4)$alkyl, $(C_3-C_4)$alkenyl, $(C_3-C_4)$alkynyl, $(C_3-C_6)$cycloalkyl, $(C_1-C_4)$-alkoxy$(C_1-C_4)$alkyl, $(C_1-C_4)$alkylthio$(C_1-C_4)$alkoxycarbonyl $(C_1-C_4)$alkyl or a $(C_4-C_5)$alkylene chain which links the nitrogen atom (3) to the carbon atom (4) of the imidazolinone or imidazoline thione ring and in which one $CH_2$ group may be substituted by oxygen or sulfur and which may be up to disubstituted by $(C_1-C_4)$alkyl, $(C_1-C_4)$alkoxycarbonyl, $(C_1-C_4)$alkoxy$(C_1-C_4)$alkoxycarbonyl or $(C_1-C_4)$alkoxycarbony $(C_1-C_4)$alkoxycarbonyl;

$R^6$ denotes hydrogen or $(C_1-C_4)$alkyl, and $R^7$ denotes $(C_1-C_8)$alkyl; phenyl or benzyl, which may in each case be up to trisubstituted by halogen, $(C_1-C_4)$alkyl, $(C_1-C_4)$alkoxy, $CF_3$, $NO_2$ or $(C_1-C_4)$alkoxycarbonyl, with the proviso that $R^2$ and $R^3$ may not denote H, halogen, $(C_1-C_4)$alkyl, $CF_3$, $(C_1-C_4)$alkoxy, phenoxy, chlorophenoxy or benzyloxy when $R^5$ represents $CH_3$, X represents oxygen and $R^1$ represents hydrogen.

Preferred compounds of the formula I are those in which $R^2$ denotes fluorine, chlorine, bromine, $(C_1-C_4)$alkoxy, halo$(C_1-C_4)$alkoxy, $(C_1-C_4)$alkylthio, $(C_1-C_4)$alkylsulfinyl, $(C_1-C_4)$alkylsulfonyl or $NO_2$;

$R^3$ denotes hydrogen, chlorine, bromine, $(C_1-C_4)$alkyl, halo$(C_1-C_4)$alkyl, $(C_1-C_4)$alkoxy, halo$(C_1-C_4)$alkoxy, $(C_3-C_4)$alkynyloxy, $(C_1-C_4)$alkylthio, $(C_1-C_4)$alkoxycarbonyl $(C_1-C_4)$alkylthio or $(C_1-C_4)$alkoxycarbonyl$(C_1-C_4)$alkoxy;

$R^4$ denotes hydrogen, $(C_1-C_4)$alkyl, benzyl, which is mono- to trisubstituted by halogen or $(C_1-C_4)$alkyl, denotes

—C—NHR$^7$,
‖
O $R^5$ denotes $(C_1-C_4)$alkyl or butylene, where one $CH_2$ group may be replaced by oxygen or sulfur and which may be up to disubstituted by $(C_1-C_4)$alkyl, $R^6$ denotes H, and $R^7$ denotes $(C_1-C_4)$alkyl.

If $R^5$ denotes a $(C_4-C_5)$alkylene chain in which one $CH_2$ group is substituted by O or S, the $-CH_2-CH_2-O-CH_2-$ or $-CH_2-CH_2-S-CH_2-$ radical, which may be substituted by $(C_1-C_4)$alkyl, is particularly suitable.

Particularly preferred compounds of the formula I are to be regarded as those in which $R^1$ denotes F, $R^2$ denotes F, Cl, Br, $(C_1-C_4)$alkoxy, halo$(C_1-C_4)$alkoxy, $(C_1-C_4)$alkylthio or $(C_1-C_4)$alkylsulfonyl; $R^3$ denotes $(C_1-C_4)$alkoxy, halo$(C_1-C_4)$alkoxy, $(C_1-C_4)$alkylthio, $(C_1-C_4)$alkoxycarbonyl$(C_1-C_4)$alkoxy, $(C_1-C_4)$alkoxycarbonyl$(C_1-C_4)$alkylthio or propargyloxy, $R^4$ denotes H, $R^5$ denotes $(C_1-C_4)$alkyl, $-CH_2-CH_2-CH_2-CH_2-$,

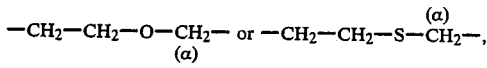
$-CH_2-CH_2-O-CH_2-$ or $-CH_2-CH_2-S-CH_2-$,   (α)

where the last three radicals may be mono- or disubstituted by $(C_1-C_4)$alkyl and the α carbon atom of these radicals is linked to carbon atom (4) of the imidazolinone or imidazoline thione ring, and $R^6$ denotes H.

The invention also covers all stereoisomers, or mixtures thereof, of the compounds of the formula I.

Haloalkyl, haloalkenyl, haloalkynyl and haloalkoxy denote that the aliphatic radicals concerned are substituted by one or more chlorine, fluorine or bromine atoms. These include, for example, $CF_3$, 1,1,2,2-tetrafluoroethoxy, 2,2-dichloro-1,1-difluoroethoxy or 2-chloro-1,1,2-trifluoroethoxy, $-O-C(Cl)=CHCl$, $-OCF_2-CFBrH$, $-O-CF_2-CH_2-Cl$, $-OCF_2-CFH-CF_3$, $-CF_2CL$, $-CF_2CHF_2$, $-CH_2CF_3$, $-CF_2CHFCL$ and $-CF_2CHF-CF_3$.

The application further relates to processes for the preparation of the compounds of the formula I, wherein a compound of the formula II is reduced, and the compounds I, having $R^4$=hydrogen, thus obtained are esterified, if desired, on the oxygen to form the other compounds of the formula I.

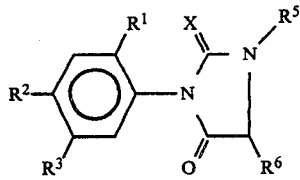

Metal hydrides, such as, for example, lithium aluminum hydride or sodium borohydride, preferably serve as reducing agents for this reaction. The reduction is carried out using sodium borohydride in a lower alcohol, an alcohol/water mixture, or an ether, such as, for example, tetrahydrofuran, diethyl ether or dimethoxyethane, as solvent. When using lithium aluminum hydride, the reaction is carried out in anhydrous ether, such as THF or dimethoxyethane.

The temperatures for the reduction are 0°–80° C., preferably 10°–40° C.

The esterification of the compounds I, having $R^4$=OH, may be carried out using an appropriate alkylating agent in the presence of an inorganic base, such as, for example, potassium carbonate, alkali metal hydroxide or sodium hydride, or in the presence of an organic base, such as, for example, triethylamine or pyridine. The reaction temperatures may be varied between room temperature and the boiling point of the solvent. Suitable solvents here are all organic solvents which are inert under the reaction conditions. Examples which may be mentioned are: toluene, acetonitrile, dimethylformamide and acetone.

Furthermore, the compounds I (R=OH) may be carbamoylated using an iso(thio)cyanate in an organic solvent which is inert under the reaction conditions, such as, for example, toluene, acetone or acetonitrile, preferably in the presence of catalytic amounts of an organic base, such as, for example, triethylamine, pyridine or 1,4-diaza-bicyclo[2,2,2]octane.

Some of the starting materials of the formula II are known (EP-A No. 70,389, EP-A No. 104,532) or can be prepared from the corresponding iso(thio)cyanates and piperidine-2-carboxylic acids, or esters thereof, or N-substituted glycines in a simple manner which is known to the expert, in this respect see Beiträge zur chemischen Physiologie und Pathologie 11, p. 160.

The compounds of the formula I according to the invention have an excellent herbicidal activity against a broad spectrum of economically important monocotyledonous and dicotyledonous harmful plants. Difficult-to-combat perennial weeds which sprout from rhizomes, rootstock or other permanent organs are also well covered by the active compounds. It is unimportant here whether the substances are applied in the pre-sowing, pre-emergence or post-emergence process.

If the compounds according to the invention are applied to the soil surface before germination, either the emergence of the weed seedlings is prevented completely, or the weeds grow to the cotyledon stage, but then stop their growth and finally die completely after three to five weeks have passed. If the active compounds are applied to the green plant parts in the post-emergence process, a drastic growth cessation likewise occurs very rapidly after the treatment, and the weed plants remain at the stage of growth which is present at the time of application or they die off completely more or less quickly after a certain time, so that weed competition which is damaging for the crop plants may be eliminated at a very early stage and for a long time by the use, in this fashion, of the new agents according to the invention.

Although the compounds according to the invention have excellent herbicidal activity against monocotyledonous and dicotyledonous weeds, crop plants of economically important crops, such as, for example, wheat, barley, rye, rice, maize, sugarbeet, cotton and soya bean, are only damaged insignificantly or not at all. For these reasons, the present compounds are very well suited for the selective combating of undesired plant growth in useful agricultural plantings.

In addition, the compounds according to the invention have growth-regulating properties in the case of crop plants. They have a regulating effect on the plant metabolism and can thus be used to simplify harvesting, such as, for example, by initiating desiccation, abscission and growth compression. In addition, they are also suitable for general control and inhibition of undesired vegetative growth, without killing off the plants during this. Inhibition of the vegetative growth plays a large part in many monocotyledonous and dicotyledonous crops, since lodging can be reduced or completely prevented by this.

The agents according to the invention may be employed as wettable powders, emulsifiable concentrates, sprayable solutions, dusting agents, dressing agents, dispersions, granules or microgranules in the conventional preparations.

Wettable powders are preparations which can be dispersed uniformly in water and which contain wetting agents, for example polyoxethylated alkylphenols, polyoxethylated fatty alcohols, alkyl- or alkylphenylsulfonates, and dispersing agents, for example sodium ligninsulfonate, sodium 2,2'-dinaphthylmethane-6,6'-disulfonate, sodium dibutylnaphthalenesulfonate, or sodium oleoylmethyltaurinate, besides the active compound and in addition to a diluent or inert substance. The preparation is carried out in a conventional fashion, for example by grinding and mixing of the components.

Emulsifiable concentrates can be prepared, for example, by dissolving the active compound in an inert organic solvent, for example butanol, cyclohexanone, dimethylformamide, xylene or higher-boiling aromatics or hydrocarbons, and adding one or more emulsifiers. In the case of liquid active compounds, the solvent component may also be partly or completely omitted. The following may be used, for example, as emulsifiers: calcium salts of alkylarylsulfonic acid, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active compound with finely divided, solid substances, for example talc, natural clays, such as kaolin, bentonite, pyrophillite or diatomaceous earths.

Granules can either be prepared by atomizing the active compound onto adsorptive, granulated inert material or by applying active compound concentrates onto the surface of excipients, such as sand, kaolinite, or of granulated inert material by means of binding agents, for example polyvinyl alcohol, sodium polyacrylate, or alternatively mineral oils. Suitable active compounds may also be granulated, if desired as a mixture with fertilizers, in the fashion which is conventional for the preparation of fertilizer granules.

In wettable powders, the active compound concentration is, for example, about 10 to 90% by weight, the remainder to 100% by weight comprising conventional formulation components. In the case of emulsifiable concentrates, the active compound concentration may be about 5 to 80% by weight. Dusty formulations usually contain 5 to 20% by weight of active compound, sprayable solutions about 2 to 20% by weight. In the case of granules, the active compound content depends partly on whether the active compound is liquid or solid and on which granulation auxiliaries, fillers etc. are used.

In addition, the active compound formulations mentioned contain, if appropriate, the adhesives, wetting agents, dispersing agents, emulsifiers, penetrants, solvents, fillers or excipients which are conventional in each case.

For use, the commercially available concentrates are diluted, if appropriate, in a conventional fashion, in the case of wettable powders, emulsifiable concentrates, dispersions and, sometimes, also in the case of microgranules, for example, using water. Dusty and granulated preparations, and also sprayable solutions, are not usually diluted with further inert substances before use.

The applicational amount which is necessary varies with the external conditions, such as temperature, humidity inter alia. It may vary within broad limits, for example between 0.005 and 10.0 kg/ha or more of active substance, but is preferably between 0.01 and 5 kg/ha. Mixtures or mixed formulations with other active compounds, such as, for example, insecticides, acaricides, herbicides, fertilizers, growth regulators or fungicides, are also possible, if appropriate.

The following examples serve to illustrate the invention.

A. FORMULATIN EXAMPLES

A dusting agent is obtained by mixing 10 parts by weight of active compound and 90 parts by weight of talc or inert substance and comminuting in a hammer mill.

A wettable powder which is easily dispersible in water is obtained by mixing 25 parts by weight of active compound, 64 parts by weight of kaolin-containing quartz as inert substance, 10 parts by weight of potassium ligninsulfonate and 1 part by weight of sodium oleoylmethyltaurinate as wetting and dispersing agent, and grinding in a pin mill.

A dispersion concentrate which is easily dispersible in water is obtained by mixing 20 parts by weight of active compound with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.), and grinding in an abrasive ball mill to a fineness of below 5 microns.

An emulsifiable concentrate is obtained from 15 parts by weight of active compound, 75 parts by weight of cyclohexanone as solvent and 10 parts by weight of oxethylated nonylphenyl (10 EO) as emulsifier.

B. CHEMICAL EXAMPLES

EXAMPLE 1

3-(4-Chloro-2-fluoro-5-methoxyphenyl)-4-hydroxy-1-methylimidazolidin-2-one 27.3 g (0.10 mol) of 3-(4-chloro-2-fluoro-5-methoxyphenyl)-1-methyl-imidazolidine-2,4-dione are dissolved in 200 ml of methanol, and 5.7 g (0.15 mol) of sodium borohydride are added in portions at a rate such that the temperature increases to 30°–35° C. When the addition is complete, the mixture is stirred for a further 1 hour at 30° C. The mixture is poured into 500 ml of ice-water, and the precipitate which deposits is filtered off under suction. After drying, 25.2 g (92% of theory) of 3-(4-chloro-2-fluoro-5-methoxyphenyl)-4-hydroxy-1-methylimidazolidin-2-one are obtained in the form of colorless crystals having the melting point 138°–140° C.

EXAMPLE 2

4-Hydroxy-1-methyl-3-[3-methyl-4-(1,1,2,2-tetrafluoroethoxy)phenyl]imidazolidin-2-one 16.0 g (0.05 mol) of 1-methyl-3-[3-methyl-4-(1,1,2,2-tetrafluoroethoxy)phenyl]imidazolidine-2,4-dione are dissolved in 100 ml of isopropanol, and 2.85 g (0.075 mol) of sodium borohydride are added at a rate such that the temperature increases to 40° C. After the addition is complete, the mixture is stirred for a further 30 minutes at 40° C., and poured into 300 ml of ice-water. The mixture is extracted twice with 100 ml of methylene chloride in each case, and the combined methylene chloride phases are washed with 100 ml of water and dried over sodium sulfate. After removing the solvent by distillation, 15.4 g (96% of theory) of 4-hydroxy-1-methyl-3-[3-methyl-4-(1,1,2,2-tetrafluoroethoxy)phenyl]imidazolidin-2-one are obtained in the form of a pale yellow viscous oil.

EXAMPLE 3

1-Butyl-3-(4-chloro-2-fluoro-5-methoxyphenyl)-4-hydroxyimidazolidine 2-thione 33.3 g (0.10 mol) of 1-butyl-3-(4-chloro-2-fluoro-5-methoxyphenyl)-4-oxo-2-thioxoimidazolidine are dissolved in 300 ml of methanol, and 5.7 g (0.15 mol) of sodium borohydride are added at a rate such that the temperature increases to 30° C. When the addition is complete, the mixture is stirred for a further 30 minutes at 30° C. and poured into 800 ml of ice-water. The precipitate is filtered off under suction and dried. 31.8 g (95% of theory) of 1-butyl-3-(4-chloro-2-fluoro-5-methoxyphenyl)-4-hydroxyimidazolidine 2-thione are obtained in the form of colorless crystals having the melting point 137°–138° C.

EXAMPLE 4

3-(4-Chloro-2-fluoro-5-methoxy-phenyl)-1-methyl-4-(N-methylcarbamoyloxy)imidazolidin-2-one 27.5 g (0.10 mol) of 3-(4-chloro-2-fluoro-5-methoxyphenyl)-4-hydroxy-1-methylimidazolidin-2-one (Example 1) are dissolved in 200 ml of acetonitrile, 50 mg of diazabicyclo[2.2.2]octane are added, and 6.84 g (0.12 mol) of methyl isocyanate are added dropwise at 20° C. The mixture is stirred for 5 hours at 50° C. and the solvent is removed by distillation. The solid residue which remains is boiled up in 200 ml of ether and cooled in an ice-bath. The precipitate is filtered off under suction and dried. 31.0 g (93% of theory) of 3-(4-chloro-2- fluoro-5-methoxyphenyl)-1-methyl-4-(N-methylcarbamoyloxy)imidazolidin2-one are obtained in the form of colorless crystals having the melting point 128°-131° C.

EXAMPLE 5

4-Benzyloxy-1-methyl-3-[3-methyl-4-(1,1,2,2-tetrafluoroethoxy)phenyl]imidazolidin-2-one 16.1 g (0.05 mol) of 4-hydroxy-1-methyl-3-[3-methyl-4-(1,1,2,2-tetrafluoroethoxy)phenyl]imidazolidin-2-one are dissolved in 150 ml of acetonitrile, and 1.50 g of sodium hydride (80% strength in white oil) are added at 5° C. The mixture is stirred for 10 minutes at 5° C., and 6.40 g (0.05 mol) of benzyl chloride are subsequently added dropwise at 5° C. The mixture is stirred for 5 hours at 50°and poured into 400 ml of ice-water. The mixture is extracted twice with 100 ml of methylene chloride in each case, and the combined methylene chloride phases are washed with 100 ml of water and dried over sodium sulfate. After removing the solvent by distillation, 19.4 g (94% of theory) of 4-benzyloxy-1-methyl-3-[3-methyl-4-(1,1,2,2-tetrafluoroethoxy)-phenyl]imidazolidin-2-one are obtained in the form of a pale yellow oil.

EXAMPLE 6

8-(4-Chloro-2-fluoro-5-methoxyphenyl)-7-hydroxy-9-oxo-1,8-diazabicyclo[4.3.0]nonane 31.3 g (0.10 mol) of 8-(4-chloro-2-fluoro-5-methoxyphenyl)-7,9-dioxo-1,8-diazabicyclo[4.3.0]nonane were dissolved in 200 ml of methanol. 5.7 g (0.15 mol) of sodium borohydride were added in portions at a rate such that the temperature was kept at 30°-40° C. When the addition was complete, the mixture was stirred for a further 1 hour at 30° C. and poured into 500 ml of water. The precipitate which deposited was filtered off under suction and dried. 29.8 g (94% of theory) of 8-(4-chloro-2-fluoro-5-methoxyphenyl)-7-hydroxy-9-oxo-1,8-diazabicyclo[4.3.0]nonane were obtained in the form of colorless crystals having the melting point 155°-157° C.

EXAMPLE 7

8-(4-Chloro-2-fluoro-5-methoxyphenyl)-7-hydroxy-9-thioxo-1,8-diazabicyclo[4.3.0]nonane 32.9 g (0.10 mol) of 8-(4-chloro-2-fluoro-5-methoxyphenyl)-7-oxo-9-thioxo-1,8-diazabicyclo[4.3.0]nonane were dissolved in 250 ml of ethanol. 5.7 g (0.15 mol) of sodium borohydride were added in portions at a rate such that the temperature was kept at 30° C. When the addition was complete, the mixture was stirred for a further 30 minutes at 30° C. and poured into 600 ml of ice-water. The precipitate was filtered off under suction, dried and recrystallized from methanol. 24.9 g (75% of theory) of 8-(4-chloro-2-fluoro-5-methoxyphenyl)-7-hydroxy-9-thioxo-1,8-diazabicyclo[4.3.0]nonane were obtained in the form of colorless crystals having the melting point 208°-215° C.

The compounds in Tables IA, IB and IC below can be obtained in an analogous fashion.

TABLE 1A

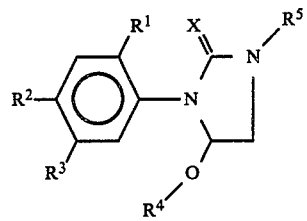

| Ex. | $R^1$ | $R^2$ | $R^3$ | $R^5$ | $R^4$ | X | m.p. [°C.] |
|---|---|---|---|---|---|---|---|
| 8 | F | Cl | $OC_2H_5$ | $n-C_4H_9$ | $CH_3$ | O | |
| 9 | F | Cl | $-OCH_3$ | $-i-C_3H_7$ | H | O | yellow oil |
| 10 | F | Cl | $-OCH_3$ | $CH_3$ | $CH_3$ | O | yellow oil |
| 11 | F | Cl | $-OCH_3$ | $CH_3$ | $-CH_2-C_6H_5$ | O | yellow oil |
| 12 | F | Cl | $-O-CH_2-CO_2C_2H_5$ | $CH_3$ | H | O | |
| 13 | F | Cl | $-OCH_2CH_2OCH_3$ | $CH_3$ | H | O | |
| 14 | F | Cl | $-SCH_3$ | $CH_3$ | H | O | |
| 15 | F | Cl | $-S-CH_2-CO_2C_2H_5$ | $CH_3$ | H | O | |
| 16 | F | Cl | $-O-i-C_3H_7$ | $CH_3$ | $-\underset{\underset{O}{\|\|}}{C}-NHCH_3$ | O | |
| 17 | F | Cl | $-OCH_3$ | $CH_3$ | $-\underset{\underset{O}{\|\|}}{C}-NHCH_3$ | S | |
| 18 | F | Cl | $-O-i-C_3H_7$ | $CH_3$ | $-\underset{\underset{O}{\|\|}}{C}-NHC_2H_5$ | S | |
| 19 | F | Cl | $-OCH_3$ | $-i-C_3H_7$ | H | S | |
| 20 | F | Cl | $-O-CH_2-CO_2C_2H_5$ | $CH_3$ | H | S | |
| 21 | F | Cl | $-O-CH_2CH_2-OCH_3$ | $CH_3$ | H | S | |
| 22 | F | Cl | $-O-CH_2-O-CH_3$ | $CH_3$ | H | S | |
| 23 | F | Cl | $-OCH_3$ | $CH_3$ | $CH_3$ | S | |
| 24 | F | Cl | $-OCH_3$ | $CH_3$ | $-CH_2-C_6H_5$ | S | |
| 25 | Cl | Cl | $-CO_2C_2H_5$ | $CH_3$ | H | O | yellow resin |
| 26 | Cl | Cl | $-CO_2C_2H_5$ | $CH_3$ | H | S | |
| 27 | H | $-OC_2H_5$ | $-CO_2C_2H_5$ | $CH_3$ | H | O | |
| 28 | H | $-OC_2H_5$ | $-CF_3$ | $-i-C_3H_7$ | H | O | |
| 29 | H | $-OCH_3$ | $-CF_3$ | $CH_3$ | H | S | |

TABLE 1A-continued

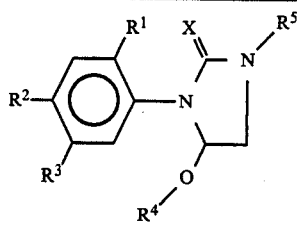

| Ex. | R¹ | R² | R³ | R⁵ | R⁴ | X | m.p. [°C.] |
|---|---|---|---|---|---|---|---|
| 30 | H | —OCH₂OCH₃ | —CF₃ | CH₃ | H | O | |
| 31 | H | —OC₂H₅ | —CN | CH₃ | H | O | |
| 32 | H | —OC₂H₅ | —NO₂ | CH₃ | H | O | |
| 33 | H | —OC₂H₅ | —CF₃ | CH₃ | H | S | |
| 34 | H | —OC₂H₅ | —CF₃ | —i-C₃H₇ | H | S | |
| 35 | H | —OC₂H₅ | —CF₃ | CH₃ | —C(=O)—NHCH₃ | S | |
| 36 | H | —OC₂H₅ | —CF₃ | CH₃ | —C(=O)—NHCH₃ | S | |
| 37 | H | —OC₂H₅ | —CF₃ | CH₃ | CH₃ | S | |
| 38 | H | —OC₂H₅ | —CF₃ | CH₃ | —CH₂—C₆H₅ | S | |
| 39 | H | —OC₂H₅ | —CF₃ | CH₃ | —i-C₃H₇ | S | |
| 40 | H | —O—CF₂—CHCl₂ | CH₃ | CH₃ | H | O | 125–126 |
| 41 | H | —O—CF₂—CHCl₂ | CH₃ | CH₃ | CH₃ | O | |
| 42 | H | —O—CF₂—CHCl₂ | CH₃ | CH₃ | —CH₂—C₆H₅ | O | |
| 43 | H | —O—CF₂—CHCl₂ | CH₃ | CH₃ | —C(=O)—NHCH₃ | O | |
| 44 | H | —OF₂—CHF₂ | CH₃ | CH₃ | H | O | yellow resin |
| 45 | H | —OF₂—CHF₂ | CH₃ | CH₃ | —CH₂—C₆H₅ | O | yellow resin |
| 46 | H | —OF₂—CHF₂ | CH₃ | CH₃ | CH₃ | O | yellow resin |
| 47 | H | —OF₂—CHF₂ | CH₃ | CH₃ | —C(=O)—NHCH₃ | O | yellow resin |
| 48 | H | —O—CF₂—CHFCl | CH₃ | CH₃ | H | O | |
| 49 | H | —OCF₃ | CH₃ | CH₃ | H | O | |
| 50 | H | —O—CCl=CHCl | CH₃ | CH₃ | H | O | |
| 51 | H | —O—CF₂—CFBrH | CH₃ | CH₃ | H | O | |
| 52 | H | —O—CH₂—CH₂Cl | CH₃ | CH₃ | H | O | |
| 53 | H | —O—CF₂—CFH—CF₃ | CH₃ | CH₃ | H | O | |

TABLE 1B

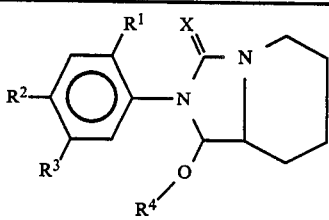

| Ex. | R¹ | R² | R³ | R⁴ | X | m.p. [°C.] |
|---|---|---|---|---|---|---|
| 54 | F | Cl | —O—i-C₃H₇ | H | O | |
| 55 | F | Cl | —O—CH₂—CO₂C₂H₅ | H | O | oil |
| 56 | F | Cl | —O—CH(CH₃)—CO₂C₂H₅ | H | O | oil |
| 57 | F | Cl | —S—CH₂—CO₂C₂H₅ | H | O | |
| 58 | F | Cl | —S—C₂H₅ | H | O | |
| 59 | F | Cl | —OCH₃ | —C(=O)—NHCH₃ | O | |
| 60 | F | Cl | —OCH₃ | —CH₂—C₆H₅ | O | |
| 61 | F | Cl | —OCH₃ | —CH₃ | O | |
| 62 | H | Br | H | H | O | 152–154 |

TABLE 1B-continued

[Structure: phenyl ring with R¹, R², R³ substituents attached via N to a piperidine-fused imidazolidine with X=C and OR⁴ group]

| Ex. | R¹ | R² | R³ | R⁴ | X | m.p. [°C.] |
|---|---|---|---|---|---|---|
| 63 | H | Br | H | —C(=O)—NHCH₃ | O | |
| 64 | H | Br | H | CH₃ | O | |
| 65 | H | —O—CF₂—CHF₂ | H | H | O | 178–180 |
| 66 | H | —O—CF₂—CHF₂ | CH₃ | H | O | |
| 67 | H | —O—CF₂—CF₂—CF₃ | CH₃ | H | O | |
| 68 | H | —O—CF₂—CHFCl | CH₃ | H | O | |
| 69 | H | —O—CF₂—CHCl₂ | CH₃ | H | O | |
| 70 | H | —OC₂H₅ | CF₃ | H | O | |
| 71 | H | —OC₂H₅ | CF₃ | —C(=O)—NHCH₃ | O | |
| 72 | H | —OC₂H₅ | —CO₂CH₃ | H | O | |
| 73 | H | —OC₂H₅ | CN | H | O | |
| 74 | H | —OC₂H₅ | NO₂ | H | O | |
| 75 | H | Cl | Cl | H | O | |
| 76 | H | CH₃ | Cl | H | O | 169–172 |
| 77 | F | F | H | H | O | |
| 78 | F | F | CO₂C₂H₅ | H | O | |
| 79 | F | Cl | —CO₂C₂H₅ | H | O | |
| 80 | Cl | Cl | —CO₂C₂H₅ | H | O | 158–160 |
| 81 | H | Cl | —OCH₃ | H | O | |
| 82 | H | Br | —OCH₃ | H | O | |
| 83 | H | Cl | —CO₂C₂H₅ | H | O | Sirup |
| 84 | H | Br | —CO₂C₂H₅ | H | O | |
| 85 | H | Cl | —CO₂C₂H₅ | —C(=O)—NHCH₃ | O | |
| 86 | F | Cl | —O—iC₃H₇ | H | S | |
| 87 | F | Cl | —OCH₃ | —C(=O)—NHCH₃ | S | |
| 88 | F | Cl | —OCH₃ | —CH₃ | S | |
| 89 | F | Cl | —OCH₃ | —CH₂—C₆H₅ | S | |
| 90 | H | Cl | —CO₂C₂H₅ | H | S | |
| 91 | H | Br | —CO₂C₂H₅ | H | S | |
| 92 | H | Br | —OCH₃ | H | S | |
| 93 | H | Cl | —OCH₃ | H | S | |
| 94 | H | Cl | H | CH₃ | O | |
| 95 | H | Cl | H | H | O | 138–143 |
| 96 | H | Cl | H | —C(=O)—NHCH₃ | O | 158–160 |
| 97 | H | Cl | —CO₂CH(CH₃)CO₂C₂H₅ | H | O | resin |
| 98 | H | —OCH₂CH₂—OCH₃ | —CF₃ | H | O | 135–137 |
| 99 | F | Br | —OCH₂C≡CH | H | O | glass |
| 100 | H | Br | —CO₂CH(CH₃)CO₂C₂H₅ | H | O | glass |
| 101 | H | F | —CO₂CH(CH₃)CO₂C₂H₅ | H | O | Sirup |
| 102 | F | Cl | —OCH₂—C≡CH | H | S | 198–204 |

TABLE 1C

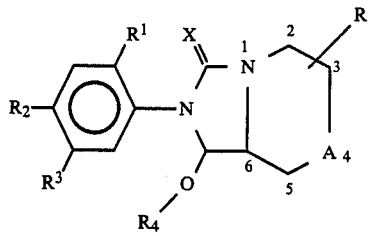

| Ex. | R$_1$ | R$_2$ | R$_3$ | R$_4$ | X | R | A | m.p. (°C.) |
|---|---|---|---|---|---|---|---|---|
| 103 | F | Cl | —OCH$_3$ | H | O | 2-CH$_3$ | CH$_2$ | glass |
| 104 | F | Cl | —OCH$_2$—C≡CH | H | O | 2-CH$_3$ | CH$_2$ | glass |
| 105 | F | Cl | —CO$_2$CH(CH$_3$)CO$_2$C$_2$H$_5$ | H | O | 2-CH$_3$ | CH$_2$ | glass |
| 106 | F | Cl | —O—CH(CH$_3$)CO$_2$C$_2$H$_5$ | H | O | 2-CH$_3$ | CH$_2$ | glass |
| 107 | H | Cl | —CO$_2$C$_2$H$_5$ | H | O | 2-CO$_2$CH(CH$_3$)CO$_2$C$_2$H$_5$ | CH$_2$ | glass |
| 108 | F | Cl | —OCH$_3$ | H | O | 3-CO$_2$C$_2$H$_5$ | CH$_2$ | glass |
| 109 | F | Cl | —OCH$_3$ | H | O | 5-C$_2$H$_5$ | CH$_2$ | sirup |
| 110 | F | Cl | —OCH$_3$ | H | O | 6-CH$_3$ | CH$_2$ | resin |
| 111 | H | Cl | H | H | O | 2-CH$_3$ | S | resin |
| 112 | F | Cl | —OCH$_3$ | H | O | H | S | 139–144 |
| 113 | F | Cl | —OCH(CH$_3$)CO$_2$C$_2$H$_5$ | H | O | H | S | glass |
| 114 | F | Cl | —OCH$_3$ | H | S | H | S | 184–188 |
| 115 | F | Cl | —OCH$_3$ | H | O | H | O | glass |
| 116 | F | Cl | —OCH$_3$ | H | S | H | O | resin |

Biological Examples

The damage to weed plants or the crop plant compatibility was assessed according to a key, in which the effectiveness is expressed by values from 0–5. In this:
0=no action or damage
1=0–20% action or damage
2=20–40% action or damage
3=40–60% action or damage
4=60–80% action or damage
5=80–100% action or damage

1. Pre-emergent action on weeds

Seeds or rhizome pieces of monocotyledonous and dicotyledonous weed plants were placed in sandy loam in plastic pots ($\phi$=9 cm) and covered with soil. The compounds according to the invention, formulated in the form of wettable powders or emulsion concentrates, were then applied in varying dosages to the surface of the covering soil as aqueous suspensions or emulsions with an applicational amount of water equivalent to 600–800 l/ha.

After treatment, the pots were placed in a greenhouse and kept under good growth conditions for the weed plants (temperature 23 plus/minus 1° C., relative air humidity 60–80%).

The optical assessment of the plants or emergence damage in comparison to the untreated controls was carried out after emergence of the test plants after an experimental time of 3–4 weeks.

As the assessment values in Table 2 show, the compounds according to the invention have a good herbicidal preemergence activity against a broad spectrum of weed grasses and weeds.

2. Post-emergent action against weeds

Seeds or rhizome pieces of monocotyledonous and dicotyledonous weeds were placed in sandy loam in plastic pots ($\phi$=9 cm), covered with soil, and germinated in a greenhouse under good growth conditions. The test plants were treated at the three-leaf stage three weeks after sowing.

The compounds according to the invention, formulated as wettable powders or as emulsion concentrates, were sprayed onto the green plant parts in various dosages having an applicational amount of water equivalent to 600 l/ha, and the action of the preparations was assessed optically in comparison to untreated controls after the test plants had stood for about 3–4 weeks in a greenhouse under optimum growth conditions (temperature 23 plus/minus 1° C., relative air humidity 60–80%).

The agents according to the invention also have a good post-emergent herbicidal activity against a broad spectrum of economically important weed grasses and weeds (Table 3).

TABLE 2

Pre-emergent action of the compounds

| Ex. | Dose (kg of i.a./ha) | herbicidal action | | | |
|---|---|---|---|---|---|
| | | SIA | CRS | ECG | LOM |
| 1 | 2,5 | 5 | 5 | 5 | 5 |
| 5 | 2,5 | 4 | 5 | 5 | 4 |
| 7 | 2,5 | 5 | 5 | 5 | 5 |
| 8 | 2,5 | 4 | 4 | 2 | 3 |
| 3 | 2,5 | 5 | 3 | 3 | 4 |
| 6 | 2,5 | 5 | 5 | 5 | 5 |
| 2 | 2,5 | 5 | 5 | 5 | 5 |
| 4 | 2,5 | 4 | 5 | 5 | 4 |
| 9 | 2,5 | 5 | 5 | 5 | 5 |
| 10 | 2,5 | 5 | 5 | 2 | 3 |
| 99 | 2,5 | 5 | 5 | 5 | 5 |
| 112 | 2,5 | 4 | 4 | 3 | 4 |

TABLE 3

Post-emergent action of the compounds

| Ex. | Dose (kg of i.a./ha) | herbicidal action | | | |
|---|---|---|---|---|---|
| | | SIA | CRS | ECG | LOM |
| 7 | 2,5 | 4 | 3 | 5 | 3 |
| 3 | 2,5 | 5 | 5 | 4 | 2 |
| 6 | 2,5 | 5 | 5 | 5 | 4 |
| 2 | 2,5 | 5 | 5 | 5 | 4 |
| 5 | 2,5 | 5 | 1 | 5 | 2 |
| 9 | 2,5 | 5 | 5 | 4 | 4 |
| 55 | 2,5 | 4 | 3 | 2 | 2 |
| 99 | 2,5 | 5 | 5 | 5 | 5 |

TABLE 3-continued

| | Post-emergent action of the compounds | | | |
|---|---|---|---|---|
| | Dose | herbicidal action | | |
| Ex. | (kg of i.a./ha) | SIA | CRS | ECG | LOM |
| 112 | 2,5 | 5 | 3 | 3 | 4 |

Abbreviations
SIA = *Sinapis alba*
CRS = *Chrysanthemum segetum*
ECG = *Echinochloa crus-galli*
LOM = *Lolium multiflorum*
a.i. = active substance

3. Crop plant compatibility

In further experiments in the greenhouse, seeds of a relatively large number of crop plants were placed in sandy loam in pots and covered with soil.

Some of the pots were treated immediately as described under 1.; the others were placed in a greenhouse until the plants had developed two to three true leaves and were then sprayed with the substances according to the invention in various dosages, as described under 2.

By means of visual assessment, it was determined, four to five weeks after the application and standing in the greenhouse, that the compounds according to the invention did not damage dicotyledonous crops, such as, for example, soya bean, cotton, rape, sugar beet and potatoes, using the pre- and post-emergent method, even at high active compound dosages. In addition, some substances also protected gramineous crops, such as, for example, barley, sorghum, maize, wheat or rice. The compounds of the formula I thus have a high selectivity when used for combating undesired plant growth in agriculturally important crops.

4. Herbicidal action when used in rice

Nodules and rhizomes or young plants or seeds of rice and various rice weeds, such as Cyperus species, Eleocharis, Scirpus and Echinochloa, were placed or planted in special rice soil in sealed pots of diameter 13 cm, and dammed with water to a level of 1 cm above the soil. The same procedure was followed with rice plants.

The compounds according to the invention, in the form of aqueous suspensions or emulsions, were poured into the watering water or, as granules, scattered into the water in the pre-emergent method, i.e. 3–4 days after planting.

In the post-emergent method, the treatment described was carried out at the three-leaf stage of the weeds and of the rice.

The herbicidal action and any damage to rice was assessed three weeks later in each case. The results showed that the compounds according to the invention are suitable for the selective combating of weeds in rice.

Compared to rice herbicides hitherto, the compounds according to the invention are distinguished in that they effectively combat numerous weeds which germinate from permanent organs, particularly those which are difficult to combat, and are tolerated by rice during this.

We claim:

1. A compound of the formula I

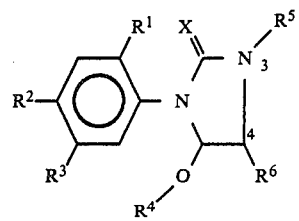

in which

X denotes oxygen or sulfur;

$R^1$ denotes hydrogen or halogen;

$R^2$ and $R^3$, independently of one another, denote hydrogen, halogen, $(C_1-C_4)$alkyl, halo$(C_1-C_4)$alkyl, $(C_1-C_4)$alkoxy, halo$(C_1-C_4)$alkoxy, $(C_3-C_6)$cycloalkoxy, $(C_2-C_4)$alkenyloxy, halo$(C_2-C_4)$alkenyloxy, $(C_5-C_6)$cycloalkenyloxy, $(C_3-C_4)$alkynyloxy, halo$(C_3-C_4)$alkynyloxy, $(C_1-C_4)$alkoxy$(C_1-C_4)$alkoxy; $(C_1-C_4)$alkoxycarbonyl$(C_1-C_4)$alkoxycarbonyl, halo$(C_1-C_4)$alkoxycarbonyl, $(C_1-C_4)$alkylsulfinyl, $(C_1-C_4)$alkylsulfonyl, phenoxy, phenylthio, phenylsulfinyl or phenylsulfonyl, where the phenyl ring may in each case be mono- to trisubstituted by halogen, $(C_1-C_4)$alkyl, $CF_3$ or $NO_2$; pyridyloxy which may be mono- or disubstituted by halogen or $CF_3$; benzyloxy or phenoxymethyl, which may both be mono- to trisubstituted in the phenyl ring by halogen, $(C_1-C_4)$alkyl, $(C_1-C_4)$alkoxy, $CF_3$ or $NO_2$; $(C_1-C_4)$alkoxycarbonyl, $(C_1-C_4)$alkoxycarbonyl$(C_1-C_4)$alkoxy, $(C_1-C_4)$alkylthio, $(C_1-C_4)$alkoxycarbonyl$(C_1-C_4)$alkylthio, $NO_2$ or CN, $R^4$ denotes hydrogen, $(C_1-C_4)$alkyl, halo$(C_1-C_4)$alkyl, $(C_3-C_4)$-alkenyl, $(C_3-C_4)$cycloalkyl, $(C_5-C_6)$-cycloalkenyl, $(C_3-C_4)$alkynyl, $(C_1-C_4)$alkoxy-$(C_1-C_4)$alkoxy, $(C_1-C_4)$alkoxycarbonyl$(C_1-C_4)$alkyl, $(C_1-C_4)$alkylthio$(C_1-C_4)$alkyl; benzyl, which may be mono- to trisubstituted by halogen, $(C_1-C_4)$alkyl, $(C_1-C_4)$alkoxy, $(C_1-C_4)$alkoxycarbonyl, $CF_3$, $NO_2$ or CN, or denotes a radical of the formula

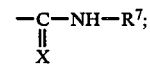

$R^5$ denotes a $(C_4-C_5)$alkylene chain which links the nitrogen atom (3) to the carbon atom (4) of the imidazolinone or imidazoline thione ring and in which one $CH_2$ group may be substituted by oxygen or sulfur and which may be up to disubtituted by $(C_1-C_4)$alkyk, $(C_1-C_4)$-alkoxycarbonyl, $(C_1-C_4)$alkoxy$(C_1-C_4)$alkoxycarbonyl or $(C_1-C_4)$alkoxycarbonyl$(C_1-C_4$alkoxycorbonyl;

$R^6$ denotes hydrogen or $(C_1-C_4)$alkyl, and $R^7$ denotes $(C_1-C_8)$alkyl; phenyl or benzyl, which may in each case be up to trisubtituted by halogen, $(C_1-C_4)$alkyl, $(C_1-C_4)$alkoxy, $CF_3$, $NO_2$ or $(C_1-C_4)$alkoxycarbonyl.

2. A compound of the formula I as claimed in claim 1, in which $R^2$ denotes fluorine, chlorine, bromine, $(C_1-C_4)$alkoxy, halo$(C_1-C_4)$alkoxy, $(C_1-C_4)$alkylthio, $(C_1-C_4)$alkylsulfinyl, $(C_1-C_4)$alkylsulfonyl or $NO_2$;

$R^3$ denotes hydrogen, chlorine, bromine, $(C_1-C_4)$alkyl, halo$(C_1-C_4)$alkyl, $(C_1-C_4)$alkoxy, halo$(C_1-C_4$ )alkoxy, (C$_3$-C$_4$)alkynyloxy, (C$_1$-C$_4$)alkylthio, (C$_1$-C$_4$)alkoxycarbonyl(C$_1$-C$_4$)alkylthio or (C$_1$-C$_4$)alkoxycarbonyl(C$_1$-C$_4$)alkoxy;

R$^4$ denotes hydrogen, (C$_1$-C$_4$)alkyl, benzyl, which is mono- to trisubstituted by halogen or (C$_1$-C$_4$)alkyl, or denotes

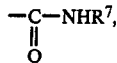

R$^5$ denotes butylene, where one CH$_2$ group may be replaced by oxygen or sulfur and which may be up to disubstituted by (C$_1$-C$_4$)alkyl, R$^6$ denotes H, and R$^7$ denotes (C$_1$-C$_4$)alkyl.

3. A compound of the formula I as claimed in claim 1, in which R$^1$ denotes F, R$^2$ denotes F, Cl, Br, (C$_1$-C$_4$)alkoxy, halo(C$_1$-C$_4$)alkoxy, (C$_1$-C$_4$)alkylthio or (C$_1$-C$_4$)alkylsulfonyl; R$^3$ denotes (C$_1$-C$_4$)alkoxy, halo(C$_1$-C$_4$)alkoxy, (C$_1$-C$_4$)alkylthio, (C$_1$-C$_4$)-alkoxycarbonyl(C$_1$-C$_4$)alkoxy, (C$_1$-C$_4$)alkoxycarbonyl-(C$_1$-C$_4$)alkylthio of propargyloxy, R$^4$ denotes H, R$^5$ denotes —CH$_2$—CH$_2$—CH$_2$—CH$_2$—, $$-CH_2-CH_2-\overset{(\alpha)}{O-CH_2}- \text{ or } -CH_2-CH_2-\overset{(\alpha)}{S-CH_2}-,$$

it being possible for the last three radicals to be mono- or disubstituted by (C$_1$-C$_4$)alkyl and the ($\alpha$) carbon atom of these radicals being linked to carbon atom (4) of the imidazolinone or imidazoline thione ring, and R$^6$ denotes H.

4. An herbicidal agent which contains an effective amount of the compound of formula I of claim 1, in a carrier.

5. A process for combating undesired plants, wherein an effective amount of a compound of the formula I of claim 1 is applied to the cultivated areas to be treated or to the plants.

* * * * *

UNITED STATES PATENT AND TRADEMARK OFFICE
CERTIFICATE OF CORRECTION

PATENT NO. : 4,749,403

DATED : June 7, 1988

INVENTOR(S) : Liebl et al.

It is certified that error appears in the above-identified patent and that said Letters Patent is hereby corrected as shown below:

Column 16, lines 37 and 38, "$(C_1-C_4)$alkoxy-$(C_1-C_4)$alkoxy should be --$(C_1-C_4)$alkoxy-$(C_1-C_4)$alkyl--;

line 54, "$(C_1-C_4)$alkyk" should be --$(C_1-C_4)$alkyl--;

line 56, "ycarbonyl($C_1-C_4$alkoxycorbonyl" should be --ycarbonyl-$(C_1-C_4)$alkoxycarbonyl--;

Column 18, line 2, "of" should be --or--.

Signed and Sealed this

Twenty-first Day of February, 1989

Attest:

DONALD J. QUIGG

Attesting Officer

Commissioner of Patents and Trademarks